United States Patent
Ning et al.

(10) Patent No.: US 10,675,333 B2
(45) Date of Patent: Jun. 9, 2020

(54) INFUSION PUMP

(71) Applicants: Guang Ning, Shanghai (CN); Weiqing Wang, Shanghai (CN); Shouyue Sun, Shanghai (CN)

(72) Inventors: Guang Ning, Shanghai (CN); Weiqing Wang, Shanghai (CN); Shouyue Sun, Shanghai (CN); Jun Shi, Shanghai (CN)

(73) Assignees: Guang Ning, Shanghai (CN); Weiqing Wang, Shanghai (CN); Shouyue Sun, Shanghai (CN)

( * ) Notice: Subject to any disclaimer, the term of this patent is extended or adjusted under 35 U.S.C. 154(b) by 104 days.

(21) Appl. No.: 15/609,679

(22) Filed: May 31, 2017

(65) Prior Publication Data
US 2017/0340821 A1    Nov. 30, 2017

(30) Foreign Application Priority Data
May 31, 2016  (CN) .......................... 2016 1 0379147

(51) Int. Cl.
*A61M 5/172*   (2006.01)
*A61K 38/24*   (2006.01)
*A61M 5/142*   (2006.01)

(52) U.S. Cl.
CPC .......... *A61K 38/24* (2013.01); *A61M 5/14216* (2013.01); *A61M 5/14228* (2013.01);
(Continued)

(58) Field of Classification Search
CPC ...... A61M 2205/33; A61M 2205/3331; A61M 2205/3365; A61M 2205/3379;
(Continued)

(56) References Cited

U.S. PATENT DOCUMENTS

| | | | |
|---|---|---|---|
| 5,180,711 A * | 1/1993 | Hodgen ................. | A61K 38/09 514/10.1 |
| 2013/0317436 A1* | 11/2013 | Ning .................... | A61M 5/1456 604/152 |

OTHER PUBLICATIONS

Zitmann, et al, Hormone substitution in male hypogonadism, Molecular and Cellular Endocrinology 161 (2000), 73-88. (Year: 2000).*

* cited by examiner

*Primary Examiner* — Laura A Bouchelle
(74) *Attorney, Agent, or Firm* — Muncy, Geissler, Olds & Lowe, P.C.

(57) ABSTRACT

An infusion pump is disclosed comprising control unit, container, actuation unit and detection unit. The container can store medicinal liquid for treating hypogonadotropic hypogonadism. The control unit can receive external control signal comprising infusion interval, concentration of medicinal liquid and dose of medicament for treating hypogonadotropic hypogonadism at each infusion. The control unit is configured to activate actuation unit based on infusion interval to cause medicinal liquid to flow out of container. The detection unit can detect output of medicinal liquid from container and feed it back to control unit. The control unit is configured to activate actuation unit based on dose at each infusion, concentration of medicinal liquid and fed-back output of medicinal liquid. According to the invention, sustained, automatic infusions of the medicament for treating hypogonadotropic hypogonadism are allowed without patient intervention. As a result, intelligent infusion of medicament is achieved in an easy and efficient manner.

14 Claims, 4 Drawing Sheets

(52) U.S. Cl.
CPC ............ *A61M 2005/14208* (2013.01); *A61M 2205/3331* (2013.01); *A61M 2205/3365* (2013.01); *A61M 2205/50* (2013.01); *A61M 2205/52* (2013.01)

(58) Field of Classification Search
CPC .......... A61M 2205/50; A61M 2205/52; A61M 5/145; A61M 2005/14208
See application file for complete search history.

INFUSION PUMP

TECHNICAL FIELD

The present invention relates to the field of medical devices and, in particular, to an infusion pump.

BACKGROUND

Hypogonadism means diminished functional activity of the gonads caused by deficient secretion and/or effects of sex hormones. This disease can be caused by a variety of reasons and is usually categorized by where the defect is as well as by the level of gonadotropin into the following two classes:

1. hypergonadotropic hypogonadism, caused by gonadal diseases and associated with compensatory increases in follicle-stimulating hormone (FSH) and luteinizing hormone (LH); and 2. hypogonadotropic hypogonadism, caused by deficient pituitary secretion of FSH and/or LH and leading to secondary gonadal dysfunction.

In clinical practices, patients with diminished gonadal function are usually treated by subcutaneous/intramuscular injection of human menopausal gonadotropins (abbreviated hereinafter as HMG). Because HMG is extracted from the urine of postmenopausal women and contains FSH and LH, hence it can improve the levels of the hormones in patients, achieving the purpose of treatment.

At present, HMG is delivered by manual injection which requires the patients to learn how to perform the injections and to always be aware of when they should perform the injections. This leads to inconvenience in the patients' daily live and learning activities. Moreover, since the conventional treatment fails to simulate the human body's natural hormone secretion behavior, long-term use of it may end in secondary failure, causing unsatisfactory efficacy of clinical treatment.

SUMMARY OF THE INVENTION

It is an object of the present invention to provide an infusion pump which is capable of not only enhancing the convenience of infusing a medicament for treating hypogonadotropic hypogonadism (e.g., HMG) by infusing it in an automatic manner but also allowing time saving of infusion, effective regulation of hormone levels in patients and better treatment effects for users.

In order to achieve the above purpose and the other related objects, the present invention provides an infusion pump, comprising: a control unit, a container, an actuation unit and a detection unit, the control unit coupled to each of the actuation unit and the detection unit, the container coupled to each of the actuation unit and the detection unit.

The container is configured to store a medicinal liquid containing a medicament for treating hypogonadotropic hypogonadism. The control unit is configured to receive an external control signal which comprises an infusion interval, a concentration of the medicinal liquid and a dose of the medicament at each infusion. The control unit performs control based on the infusion interval such that the actuation unit is activated to cause the medicinal liquid to flow out of the container. The detection unit is configured to detect an output of the medicinal liquid from the container and feed it back to the control unit. The control unit is configured to deactivate the actuation unit based on the dose of the medicament at each infusion, the concentration of the medicinal liquid and the fed-back output of the medicinal liquid.

Preferably, the medicament for treating hypogonadotropic hypogonadism is human menopausal gonadotropins; the medicinal liquid is a medicinal liquid of human menopausal gonadotropins; the infusion interval for the medicinal liquid of human menopausal gonadotropins is 90-120 minutes; the dose of human menopausal gonadotropins at each infusion is 0.04-0.2 µg/kg of body weight; and the concentration of the medicinal liquid of human menopausal gonadotropins is 75-225 µg/ml.

Preferably, the infusion interval for the medicinal liquid of human menopausal gonadotropins is 90 minutes; the dose of human menopausal gonadotropins at each infusion is 0.1-0.2 µg/kg of body weight; and the concentration of the medicinal liquid of human menopausal gonadotropins is 150-225 µg/ml.

Preferably, the actuation unit comprises a DC motor and a transmission mechanism; an outlet is provided on one end of the container and a piston is provided in the container; one end of the transmission mechanism is coupled to the piston and the other end is coupled to the DC motor; the transmission mechanism is configured to convert rotation motion of the DC motor to linear motion of the piston; and the piston is configured to move toward the outlet so that the medicinal liquid in the container is discharged from the outlet.

Preferably, the detection unit comprises a detection device for counting the number of rotations of the DC motor, which is coupled to a rotary shaft of the DC motor; the control unit calculates the number of theoretical rotations of the DC motor based on the dose of the medicament and the concentration of the medicinal liquid of the container and feed it back to the detection device for counting the number of rotations of the DC motor; and the detection device for counting the number of rotations of the DC motor controls rotations of the DC motor based on the fed-back number of theoretical rotations.

Preferably, the detection unit comprises a detection device for counting the number of rotations of the DC motor, which is coupled to a rotary shaft of the DC motor; the detection device for counting the number of rotations of the DC motor is configured to count the number of actual rotations of the DC motor and feed it back to the control unit; and the control unit calculates the number of theoretical rotations of the DC motor based on the dose of the medicament and the concentration of the medicinal liquid of the container, judges, based on the number of actual rotations, whether the DC motor reaches the number of theoretical rotations, and if the condition is met, perform control such that the DC motor is deactivated.

Preferably, the actuation unit is an expulsion device which is coupled to one end of the container where the outlet is provided and is configured to expel the medicinal liquid out of the container.

Preferably, the expulsion device is a peristaltic pump, a piezoceramic pump or a film pump.

Preferably, the detection unit comprises a pressure sensor which is coupled to the container and configured to sense a pressure resulting from the flow of the medicinal liquid in the container and to feed it back to the control unit; and the control unit obtains an output of the medicinal liquid at each time by looking up a table based on the pressure resulting from the flow of the medicinal liquid.

Preferably, the control unit, upon determining that one of the time points is reached, reads out one of the infusion doses that corresponds to the reached time point and performs control such that the actuation unit is activated to carry out an infusion action based on the read-out infusion dose; and wherein the time points for respective infusions are calculated from the infusion interval.

Preferably, concurrently with the actuation unit carrying out the infusion action, the control unit reads out a one of the infusion doses that corresponds to the next one of the time points and if the next infusion dose equals to an initial value, the control unit reads out a further next one of the infusion doses that corresponds to a further next one of the time points that is next to said next time point, this process is repeated until one of the infusion doses, which is not equal to the initial value, is found, and a corresponding one of the time points that corresponds to the infusion dose, which is not equal to the initial value, is taken as a time point for a next infusion action; and if the condition is not met, the control unit takes said next time point as a time point for the next infusion action.

Preferably, the control unit comprises a storage unit and a clock unit; the control unit judges whether any one of time points for infusion is reached based on a timing function of the clock unit and the storage unit stores the time points for respective infusions and infusion doses of the medicament corresponding to the time points; and the time points for infusion are calculated from the infusion interval.

Preferably, the control unit further comprises a predefined minimum time interval; and the infusion interval is a multiple of the minimum time interval.

Preferably, the storage unit comprises a storage table with a size of 2×n, where n is the product of dividing 24×60 by the minimum infusion interval measured in minutes; the storage table has a first row where theoretical time points for infusion are stored and a second row where initial values for the infusion doses of the medicament are stored; and upon receipt of the external control signal, the control unit converts the infusion interval to the time points for infusion, finds cells in the first row where the ones of the theoretical time points that are consistent with the converted time points for infusion are stored and writes the infusion doses in the corresponding cells in the second row of the storage table.

Preferably, the infusion pump further comprises an input unit coupled to the control unit; and the external control signal is input to the control unit through the input unit.

Preferably, the infusion pump further comprises a casing in which the control unit, the container, the actuation unit and the detection unit are accommodated.

Compared to the prior art, during use of the infusion pump of the present invention, infusions of the medicament for treating hypogonadotropic hypogonadism are carried out based on an external control signal received by the control unit and are initialized or terminated automatically by activating or deactivating of the actuation unit also based on the external control signal. Such an infusion pump allows sustained, automatic infusions of the medicament for treating hypogonadotropic hypogonadism without patient intervention. As a result, intelligent infusions of the medicament for treating hypogonadotropic hypogonadism are achieved in an easy and efficient manner.

In addition, parameters for infusions of the medicinal liquid of human menopausal gonadotropins, including the infusion interval, the dose of human menopausal gonadotropins at each infusion and the concentration of the medicinal liquid of human menopausal gonadotropins, are optimized according to the characteristics of sustained infusions, enabling more effective regulation of hormone levels in patients as well as a better treatment effect of the medicament of human menopausal gonadotropins.

Figure 1:
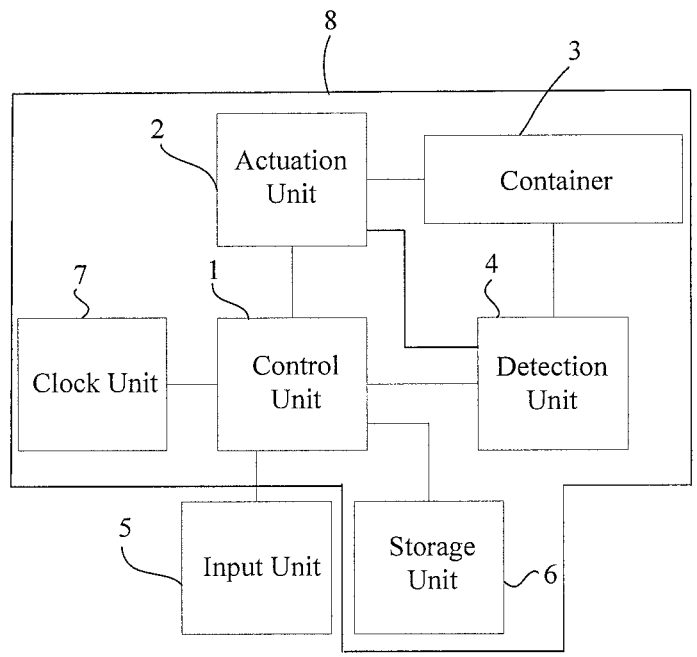
FIG. 1 is a structural block diagram of an infusion pump according to a first embodiment of the invention.

Reference numerals in the figures are as follows:
1, a control unit; 2, an actuation unit; 3, a container; 4, a detection unit; 5, an input unit; 6, a storage unit; 7, a clock unit; 8, a casing; 31, an outlet; 32, a piston; 21, a DC motor, 210, a rotary shaft; 22, a transmission mechanism; 221, a steering gear set; 222, a lead screw; 223, a nut; 224, a push rod; 23, an expulsion device; a detection device 41 for counting the number of rotations of the motor; and 42, a pressure sensor.

DETAILED DESCRIPTION

In order for the objects, advantages and features of the present invention to become more apparent, infusion pumps proposed in the present invention will be described below in greater detail with reference to FIGS. 1 to 5. It is a matter of course that the invention is not limited to the specific embodiments disclosed and general substitutions well known to those skilled in the art are also encompassed within the scope of the invention.

In addition, the accompany drawings to which the present invention is described in detail with reference are intended to facilitate the detailed description of the specific embodiment of the invention and shall not be construed as limiting the invention.

<Embodiment 1>

Provided in Embodiment 1 of the present invention is an infusion pump, as shown in FIG. 1, illustrating a structural block diagram of the infusion pump according to Embodiment 1 of the invention.

The infusion pump comprises a control unit 1, an actuation unit 2, a container 3 and a detection unit 4, wherein the control unit 1 is coupled to each of the actuation unit 2 and the detection unit 4, with the container 3 being coupled to each of the detection unit 4 and the actuation unit 2.

The container 3 is configured to store an HMG (i.e., human menopausal gonadotropins, the same applies hereinafter) medicinal liquid. The control unit 1 is configured to receive an external control signal input by a user, which comprises an infusion interval, a concentration of the HMG medicinal liquid in the container 3 and an HMG dose at each infusion. The actuation unit 2 may be activated under the control of the control unit 1 based on the infusion interval input by the user so that the HMG medicinal liquid is forced to flow out of the container 3. The detection unit 4 may detect an output of the HMG medicinal liquid from the container 3 and feed it back to the control unit 1. The actuation unit 2 may be deactivated under the control of the control unit 1 based on the HMG infusion dose input by the user, the concentration of the HMG medicinal liquid in the container 3 and the fed-back output of the HMG medicinal liquid. That is, the actuation unit 2 is deactivated upon the output amount of the HMG medicinal liquid from the container 3 reaching a predefined infusion amount.

During use, the infusion interval for the HMG medicinal liquid is so set that one infusion is performed within each period of 90-120 minutes, the HMG infusion dose is closely related to body weight and lies in the range of 0.04-0.2 µg/kg of body weight, and the concentration of the HMG medicinal liquid is 75-225 µg/ml.

During use of the infusion pump provided in this embodiment, HMG infusions are carried out based on an external control signal received by the control unit 1 and are initialized or terminated automatically by activating or deactivating of the actuation unit 2 also based on the external control signal. Compared to the manual injection approach, HMG infusions with such an infusion pump are allowed to be conducted in a sustained, automatic manner without patient intervention. As a result, intelligent HMG infusions are achieved in an easy and efficient manner. Additionally, parameters for infusions of the HMG medicinal liquid, including the infusion interval, the HMG dose at each infusion and the concentration of the HMG medicinal liquid, are optimized according to the characteristics of sustained infusions, enabling more effective regulation of hormone levels in patient as well as a higher efficacy of HMG.

Preferably, the infusion interval for the HMG medicinal liquid is set to 90 minutes, the HMG dose at each infusion to 0.1-0.2 µg/kg of body weight and the concentration of the HMG medicinal liquid to 150-225 µg/ml.

Continued reference is now made to FIG. 1, in order to facilitate the input of the external control signal, the infusion pump may also include an input unit 5 coupled to the control unit 1, with which the user can input the external control signal to the control unit 1. That is, the control unit 1 receives the external control signal via the input unit 5. The input unit 5 may comprise an input key.

In this embodiment, the control unit 1 may include a storage unit 6 for storing the external control signal. The control unit 1 may further include a clock unit 7 for accurate timing which allows the control unit 1 to activate the actuation unit 2 at scheduled time points for infusion.

In this embodiment, the infusion pump may also include a casing 8, in which the control unit 1, the actuation unit 2, the container 3 and the detection unit 4 are accommodated and secured.

Figure 2:
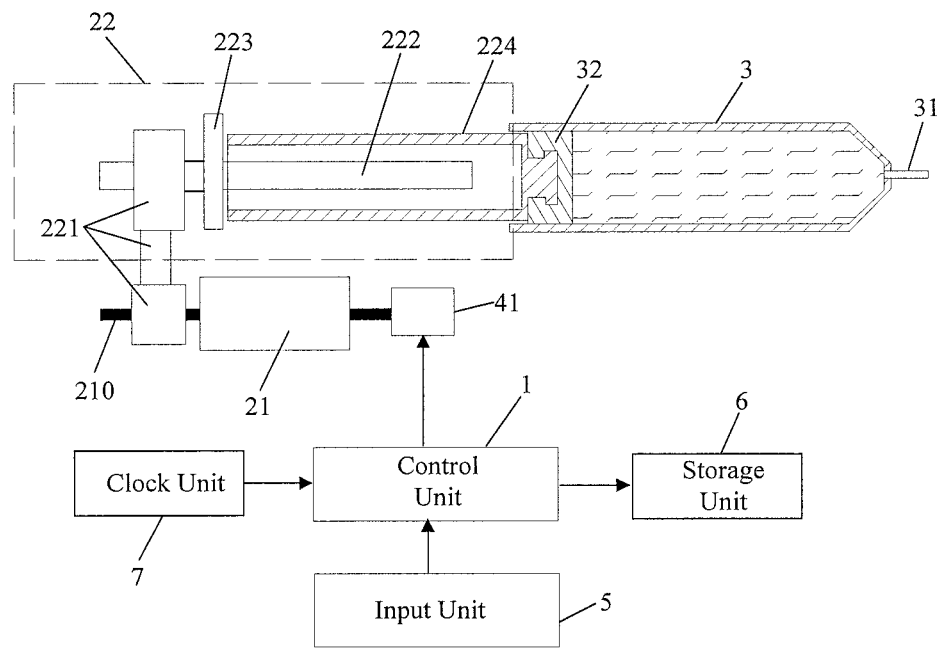
FIG. 2 is a structural schematic of the infusion pump according to the first embodiment of the invention.

Reference is further made to FIG. 2, a structural schematic of the infusion pump according to Embodiment 1 of the present invention.

As shown in FIG. 2, the actuation unit 2 may include a DC motor 21 and a transmission mechanism 22. An outlet 31 may be provided on one end of the container 3, and a piston 32 may be provided in the container 3. One end of the transmission mechanism 22 is coupled to the piston 32, and the other end is coupled to the DC motor 21. The transmission mechanism 22 is able to convert rotating motion of the DC motor 21 to linear motion of the piston 32. Upon the piston 32 moving toward the outlet 31, the HMG medicinal liquid in the container 3 may be discharged from the outlet 31. Optionally, the transmission mechanism 22 may include a steering gear set 221, a lead screw 222, a nut 223 and a push rod 224. The steering gear set 221 is coupled to both a rotary shaft 210 of the DC motor 21 and the lead screw 222 in order to transmit rotation of the rotary shaft 210 to the lead screw 222 so as to drive the lead screw 222 to rotate. The nut 223 is coupled to the casing 8 via a chute with a central axis aligned with that of the lead screw 222. That is, the nut 223 is linearly movable on the casing 8. A thread in the nut 223 mates with a thread in the lead screw 222, and the nut 223 is disposed over the lead screw 222. When the lead screw 222 rotates, it can drive the nut 223 to move forth or back on the casing 8. The push rod 224 is hollow and is fixed to the piston 32 at one end. One end of the lead screw 222 passes through the nut 223 and is inserted into the push rod 224, and the other end of the push rod 224 is brought into contact with the nut 223. As a result, when the lead screw 222 rotates and thereby drives the nut 223 to move toward the container 3, the nut 223 pushes the push rod 224 forward and hence drives the piston 32 to move within the container 3.

With continued reference to FIG. 2, the detection unit 4 may include a detection device 41 for counting the number of rotations of the motor, which is coupled to the rotary shaft 210 of the DC motor 21 and configured to count the number of actual rotations of the DC motor 21. The control unit 1 calculates the number of theoretical rotations based on the HMG infusion dose and the concentration of the HMG medicinal liquid in the container 3 and judges whether the DC motor 21 already reaches the number of theoretical rotations based on the number of actual rotations fed back from the detection unit 4. If the condition is met, the DC motor 21 is deactivated. Otherwise, the DC motor 21 continues its operation until the number of theoretical rotations is reached.

In other embodiments, the control unit 1 may further transmit the number of theoretical revolutions of the DC motor 21 to the detection device 41, and based on the received number of theoretical rotations, the detection device 41 may control the rotations of the DC motor 21 and judge whether to deactivate the DC motor 21 based on the number of theoretical rotations. In this embodiment, the control unit 1 may calculate the number of theoretical rotations of the DC motor 21 based on the HMG dose at each infusion, the concentration of the HMG medicinal liquid in the container 3, a diameter of the container 3 and a transmission ratio of the transmission mechanism 22.

Figure 3:
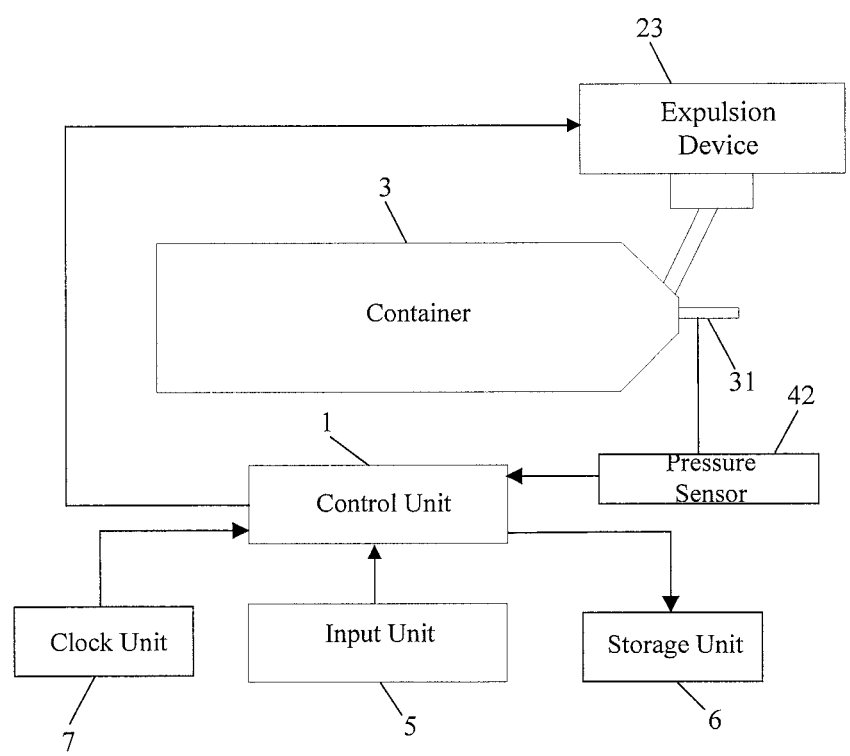
FIG. 3 is a structural schematic of another infusion pump according to the first embodiment of the invention.

Another embodiment is shown in FIG. 3, a structural schematic of another infusion pump according to Embodiment 1. The actuation unit 2 may be an expulsion device 23 which is coupled to one end of the container 3 where the outlet 31 is provided and is configured to expel the HMG medicinal liquid out of the container 3. The expulsion device 23 is preferred to be a peristaltic pump, a piezoceramic pump, a film pump, etc., with a linear peristaltic pump being more preferred. In FIG. 3, the control unit 1 is directly coupled to the expulsion device 23 so that the expulsion device 23 can be activated and deactivated under the control thereof. For the structure shown in FIG. 3, the detection unit 4 preferably includes a pressure sensor 42 which is coupled to the container 3 and the control unit 1 and is configured to detect a pressure resulting from the flow of the HMG medicinal liquid in the container 3. The pressure sensor 42 feeds the pressure to the control unit 1 which then obtains an output of HMG medicinal liquid from the container 3 by looking up a Pressure—Flow Rate table stored on the storage unit 6 so as to judge whether to stop the operation of the expulsion device 23. Specifically, the Pressure—Flow Rate table specifying data about predefined pressures and corresponding flow rates is stored in the storage unit 6.

<Embodiment 2>

Figure 4:
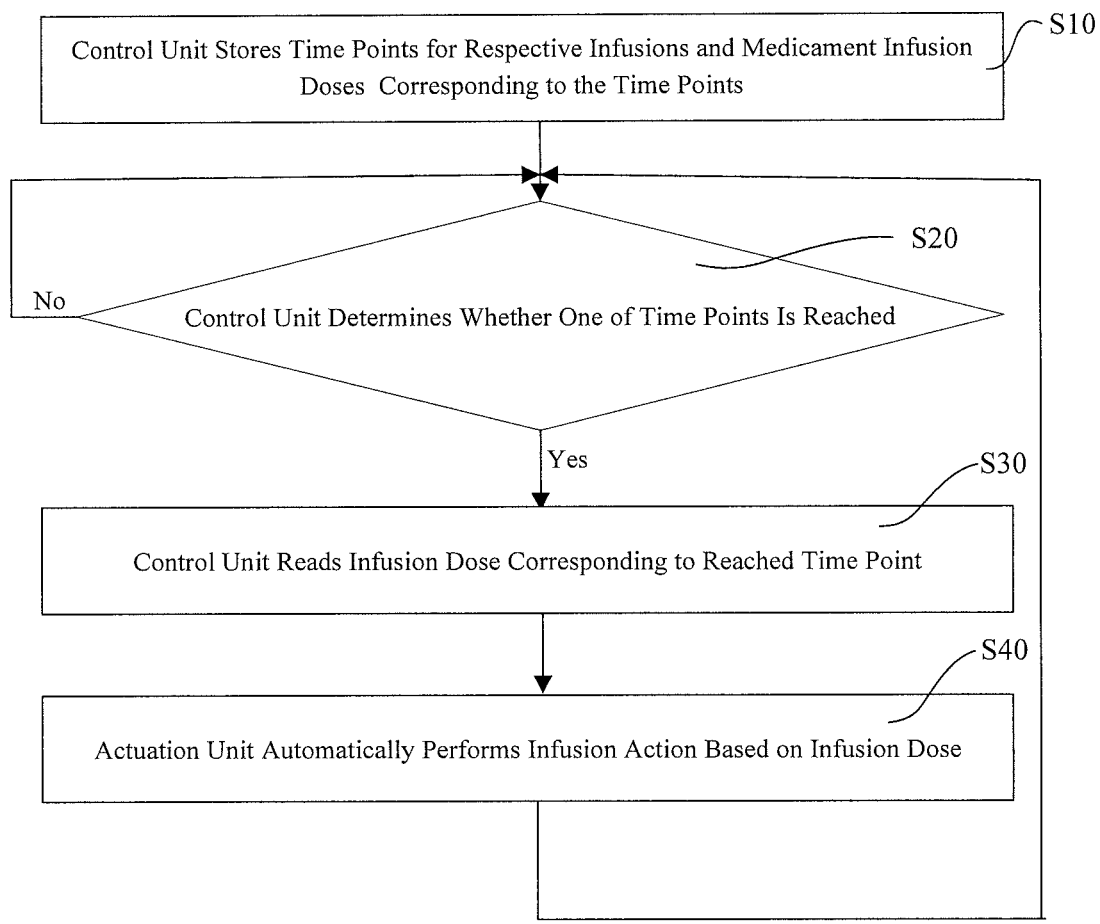
FIG. 4 is a flowchart schematically illustrating a method for operating an infusion pump according to a second embodiment of the invention.

On the basis of Embodiment 1, provided in this embodiment is a method of operating an infusion pump for infusing an HMG medicinal liquid. As shown in FIG. 4, a flowchart illustrating the method of operating the infusion pump according to Embodiment 2.

As shown in FIG. 4, the method of operating the infusion pump includes:

step S10: storing, by the control unit 1, time points for respective infusions and infusion doses of the medicament corresponding to the time points;

step S20: judging, by the control unit 1, whether one of the time points for infusion is reached, if the condition is met, proceeding to step S30, and otherwise, continuing step S20;

step S30: reading, by the control unit 1, the infusion dose corresponding to the reached time point for infusion and proceeding to step S40;

step S40: automatically performing an infusion action by the actuation unit 2 based on the corresponding infusion dose and, after the completion of the action, looping back to step S20.

In this method, once setting of the infusion pump has been completed, the control unit 1 starts to carry out the judging and reading actions, and at each of the time points for infusion, the actuation unit 2 automatically performs an infusion action.

According to this example, a minimum infusion interval is predefined to prevent the infusion pump from operating for multiple times within a short period of time due to a faulty operation of the user, which may lead to the infusion of an excessive amount of the HMG medicinal liquid and side effects on the body. Here, the minimum infusion interval may be chosen according to the accuracy of the infusion pump itself, the mechanism of action of the medicament, the concentration of the medicinal liquid and the like. Preferably, the infusion interval input by the user has to be a multiple of the minimum infusion interval. More preferably, the minimum infusion interval is 10-30 minutes.

In addition, the infusion interval input by the user may either be constant or vary with an infusion need. For example, infusions can be carried out at a fixed interval of 90 minutes or at intervals of 90 minutes, 100 minutes, 120 minutes, etc. (with an minimum infusion interval of 10 minutes as an example). The present invention is not limited in this regard.

Of course, in order to store data about the time points and the respectively corresponding infusion doses, an "Infusion Time Points-Infusion Doses" storage table specifying the time points for infusion and the respectively corresponding infusion doses may also be provided in the storage unit 6. During setting of the infusion pump, the control unit 1 may store the external control signal by using the "Infusion Time Points-Infusion Doses" storage table. During operation of the infusion pump, the control unit 1 may read time points for infusion and corresponding HMG infusion doses from the "Infusion Time Points-Infusion Doses" storage table. The size of the "Infusion Time Points-Infusion Doses" storage table may be determined based on the total number of theoretical time points for infusion. Here, the total number of theoretical time points for infusion may be equal to the product of dividing 24×60 by the minimum infusion interval (calculated based on the immutable fact that there are 24 hours in a day, with the minimum infusion interval measured in minutes), and the details are shown in Table 1.

TABLE 1

| Time Points for Infusion and Infusion Doses | | | | | | | | | | |
|---|---|---|---|---|---|---|---|---|---|---|
| 1 | 2 | 3 | 4 | 5 | 6 | 7 | 8 | — | n − 1 | n |
| Infusion Dose | 0 | 0 | Infusion Dose | 0 | Infusion Dose | 0 | 0 | — | Infusion Dose | 0 |

Table 1 shows an array of 2 rows and n columns, indicating that the user is allowed to set at most n theoretical time points for infusion and n infusion doses respectively corresponding to the n theoretical time points for infusion, where n is the product of dividing 24×60 by the minimum infusion interval. Wherein, the first theoretical time point for infusion is stored in the cell of the first row and first column and may be arbitrary. However, in order to facilitate the calculation of time points for infusion based on the user-defined time interval, the first theoretical time point for infusion is preferable selected as 0:00 a.m. and serves as a reference point. That is, the first theoretical time point for infusion may be 0:00 a.m. The second theoretical time point for infusion is stored in the cell of the first row and second column, with the second theoretical time point being staggered from the first theoretical time point by the minimum infusion interval, for example, 0:15 a.m. (with the minimum infusion interval of 15 minutes as an example), and so forth. Additionally, each of the theoretical time points for infusion corresponds to an initial infusion dose value which is, for example, zero or an unreasonable value (that is unreasonable for the infusion dose, for example, negative). In the storage table, the time points for infusion may be represented in various forms, and the present invention is not limited in this regard. For example, the time points can be represented as time format. In this case, upon the external control signal being received, the control unit 1 may calculate the time points for infusion based on the user-defined infusion interval and store the infusion doses in the respective cells in the storage table. The time points for infusion may also be represented as ordinal format as in Table 1. In this case, when to judge whether an infusion should be conducted, the value in a certain cell in the first row of Table 1 is converted into a corresponding specific time point. During setting of the infusion interval by the user, data storage by the control unit 1 starts from the first column of Table 1. If the user selects the infusion interval as the minimum time interval, the infusion dose input by the user is stored in the cell in the second row and first column. If the user selects the infusion interval as a value m times the minimum time interval (m=2, . . . , n), the control unit 1 stores the infusion dose input by the user in the cell in the second row and m-th column. Preferably, prior to the setting by the user, the initial infusion dose values corresponding to the respective theoretical time points are preset to zero. Afterward, during the setting, the user can input non-zero infusion dose values corresponding to certain theoretical time points for infusion via the input unit 5, meaning that infusions are to be carried out at these theoretical time points. After completing the setting of the infusion pump by the user, the control unit 1 takes the user-defined time point for infusion from Table 1 that is closest to the time point when the setting of the infusion pump was completed as the time point for the first infusion.

Subsequently, according to the method of operating the infusion pump shown in FIG. 4, the control unit 1 may judge whether one of the time points for infusion is reached based on the timing function of the clock unit 7. If it is indicated that one of the time points for infusion is reached, the control unit 1 accesses the storage unit 6 and reads therefrom the infusion dose corresponding to the time point, and controls the actuation unit 2 to carry out an infusion based thereon. Of course, if the infusion dose corresponding to the time point is zero, the actuation unit 2 does not perform any infusion.

Figure 5:
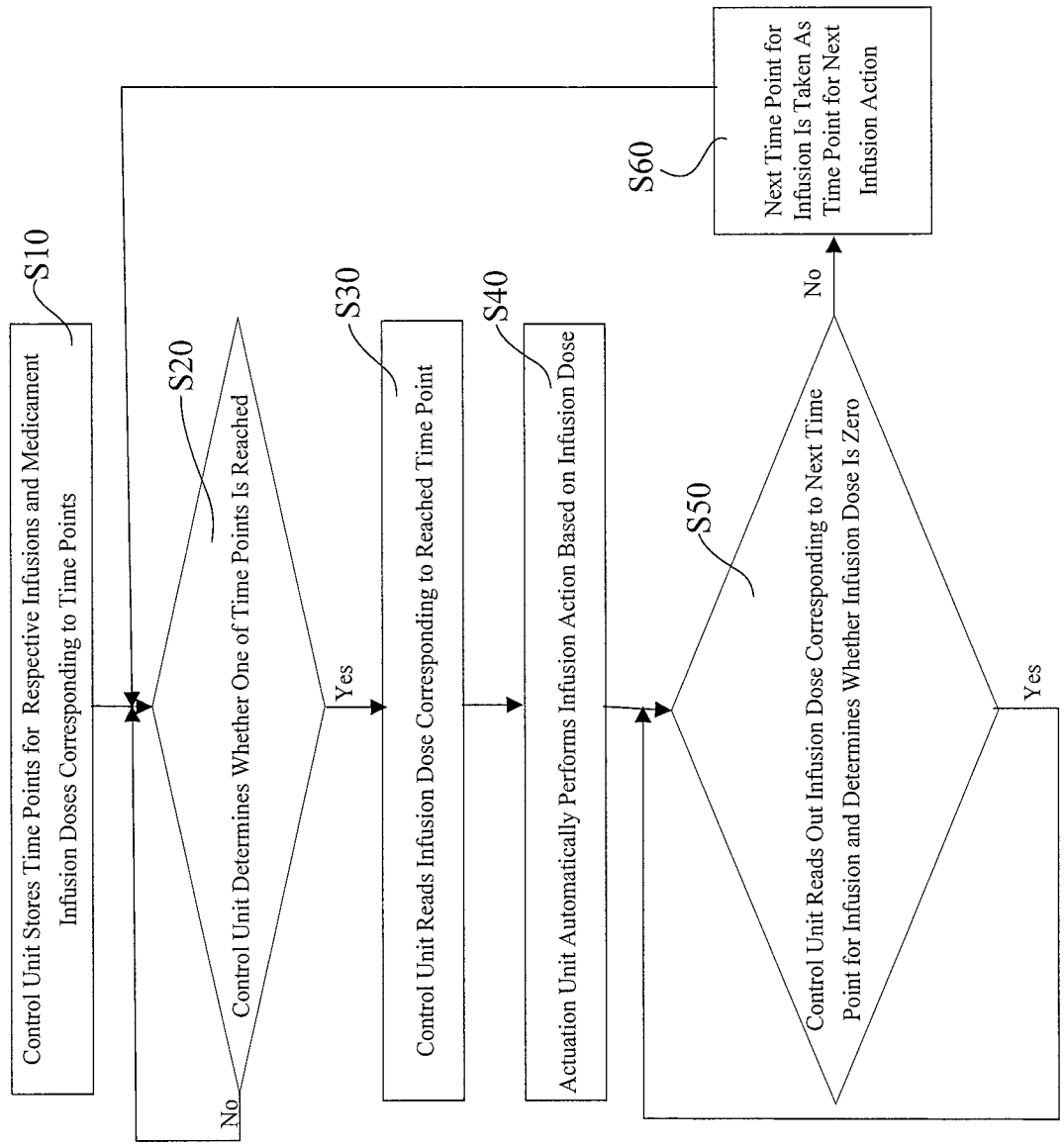
FIG. 5 is a flowchart schematically illustrating another method for operating the infusion pump according to the second embodiment of the invention.

In a preferred example, reference is made to FIG. 5, a flowchart showing another method of operating the infusion pump in accordance with Embodiment 2 of the present invention.

As shown in FIG. 5, the method of operating the infusion pump includes the following steps.

In step S10, the control unit 1 stores time points for respective infusions and infusion doses corresponding to the time points.

In step S20, the control unit 1 judges whether one of the time points for infusion is reached, if the condition is met, the method proceeds to step S30, and otherwise, step S20 is continued.

In step S30, the control unit 1 reads an infusion dose corresponding to the reached time point for infusion, and the method proceeds to step S40.

In step S40, the actuation unit 2 automatically performs an infusion action based on the corresponding infusion dose, and the method proceeds to step S50.

In step S50, the control unit 1 reads out an infusion dose corresponding to the next time point for infusion and judges whether the corresponding infusion dose is zero. If the condition is met, the method loops back to step S50, so that the control unit 1 reads out the infusion dose corresponding to the time point next to the aforementioned next time point and judges whether the infusion dose is zero. This process is repeated until a non-zero infusion dose is found, and the time point for infusion corresponding to the non-zero infusion dose is taken as the time point for the next infusion action. Otherwise, step S60 is performed.

In step S60, the next time point for infusion is taken as the time point for the next infusion action, and the method loops back to step S20.

Specifically, during the performance of each infusion action, the control unit 1 further reads out the infusion dose corresponding to the next time point for infusion. If the corresponding infusion dose is not equal to zero, then the next time point for infusion is taken as the time point for the next infusion action. As such, the only task left to the control unit 1 is to judge whether the time point for infusion is reached. If the infusion dose is zero, then the control unit 1 further reads out the infusion dose corresponding to the time point next to the aforementioned next time point. This is repeated until a non-zero infusion dose is found, and the time point corresponding to the non-zero infusion dose is taken as the time point for the next infusion action by the actuation unit 2.

In this method, similarly, upon the user having completed the setting of the infusion pump, the control unit 1 starts to carry out the judging and reading actions, and at each of the time points for infusion, the actuation unit 2 automatically performs an infusion action. Differently, in this method, during reading of the first time point for infusion, the control unit 1 further reads out the infusion dose corresponding to the time point and judges whether it is zero. If it is zero, the control unit 1 reads out the next time point for infusion and an infusion dose corresponding thereto. This process is repeated until a time point for infusion corresponding to a non-zero infusion dose is found.

In summary, in the method for operating the infusion pump shown in FIG. 4, the control unit 1 needs to judge on a regular basis whether one of the time points for infusion is reached so that one such judgement is made for each of the time points for infusion. Additionally, at each of the time points for infusion, the control unit 1 further needs to judge whether the infusion dose corresponding to the time point is zero. As a result, more such regular data reading and judging actions that will wake up the infusion pump from an energy-saving sleep mode need to be done, leading to increased power consumption and lower operating efficiency of the device.

Compared to the operating method for the infusion pump shown in FIG. 4, in the operating method for the infusion pump shown in FIG. 5, following each infusion conducted by the actuation unit 2, the infusion dose corresponding to the next time point for infusion and even those corresponding to the time points subsequent to the aforementioned time point are successively read out until a time point corresponding to the next non-zero infusion dose is reached, and this time point is taken as the time point for the next infusion action. As such, the control unit 1 does not need to perform a judgement for each of the time points on a regular basis, and each infusion action is performed concurrently with reading of at least the infusion dose corresponding to the next time point for infusion. This reduces the judging actions required to be done by the control unit 1 and allows reading of the infusion doses in a non sleep mode. Therefore, the energy consumption of the device is reduced and its operating efficiency is improved.

The results of a GnRH stimulation test are further provided in this embodiment and are presented in detail in Table 2. In the test, a female subject with a body weight of 51.5 kg was included, and her luteinizing hormone (LH) and follicle-stimulating hormone (FSH) levels were measured as test indicators both in mIU/mL.

TABLE 2

| Results of GnRH Stimulation Test | | | | | | | | | | | | |
|---|---|---|---|---|---|---|---|---|---|---|---|---|
| Time | −15 min | | 0 min | | 25 min | | 45 min | | 90 min | | 180 min | |
| Indicator | LH | FSH | LH | FSH | LH | FSH | LH | FSH | LH | FSH | LH | FSH |
| Result | 1.04 | 3.22 | 0.99 | 3.49 | 3.2 | 4.47 | 3.76 | 5.44 | 3.76 | 6.21 | 2.46 | 6.12 |
| Reference LH Level (mIU/mL) | | | | | | 0.56~14.00 | | | | | | |
| Reference FSH Level (mIU/mL) | | | | | | 1.4~5.5 | | | | | | |

As indicated by the results of the GnRH stimulation test, LH could be stimulated to a maximum level of 3.76 mIU/mL and FSH to a maximum level of 6.21 mIU/mL. That is, both of them could be stimulated. Indications for HMG treatment were confirmed in a diagnosis performed on the subject for identifying partial anterior pituitary dysfunction. Further, it can be appreciated that, in the "Time" row, 0 min represents a reference time for the test, −15 min represents a time prior to the reference time (this is the reason why it is marked with a negative sign), and all the measurements performed after the reference time are staggered by certain intervals.

The results of a HMG stimulation test for a patient with anterior pituitary dysfunction using the infusion pump according to the above embodiment are further provided in this embodiment, and the efficacy on Days 1 and 3 are shown in Table 3.

TABLE 3

Results of HMG Stimulation Test (1)

| | | Time | | | | | | |
|---|---|---|---|---|---|---|---|---|
| | | 0 min | 25 min | 45 min | 90 min | 115 min | 135 min | 300 min |
| Day 1 | LH | 1.06 | 1.01 | 1.01 | 0.91 | 0.94 | 0.90 | 1.04 |
| | FSH | 3.67 | 3.50 | 3.59 | 3.51 | 3.66 | 3.75 | 3.70 |
| Day 3 | LH | 0.82 | 1.07 | 1.07 | 0.82 | 1.03 | 1.04 | 0.94 |
| | FSH | 8.64 | 9.05 | 9.09 | 9.34 | 8.73 | 9.38 | 9.07 |

Table 3 shows the efficacy on Days 1 and 3, wherein the infusion interval for the HMG medicinal liquid was 90 min, the dose at each infusion was 10 μg (corresponding to the above-described case in which the female subject had a body weight of 51.5 kg), and the concentration of the medicinal liquid was 200 μg/ml. In addition, the efficacy after a longer duration of sustained HMG infusions is shown in Table 4.

TABLE 4

Result of HMG Stimulation Test (2)

| Duration (days) | LH | FSH | Estradiol |
|---|---|---|---|
| 34 | <0.07 | 14.78 | >1000 |
| 47 | <0.07 | 5.84 | 232 |
| 69 | 0.25 | 7.97 | <10 |
| 97 | 1 | 8.71 | <10 |
| 132 | 1.68 | 7.09 | <10 |
| 189 | 0.17 | 9.03 | 29 |

Note: in the above Table 3 and 4, LH and FSH are both measured in mIU/mL, and estradiol in pq/ml. In addition, measurement results of the patient's uterine size under the sustained infusion condition are shown in Table 5.

TABLE 5

Patient's Uterine Size (measured by ultrasound)

| Duration (days) | Length × Thickness × Width (mm × mm × mm) |
|---|---|
| 34 | 35 × 31 × 35 |
| 47 | 39 × 25 × 34 |
| 69 | 28 × 22 × 30 |
| 97 | 27 × 19 × 28 |
| 132 | 31 × 22 × 33 |
| 189 | 30 × 23 × 27 |
| Preclinical examination | 16 × 12 × 18 |

Further, as can be seen from Tables 3 and 4, HMG infusions using the infusion pump provided in this embodiment can effectively regulate the patient's follicle-stimulating hormone and luteinizing hormone levels and thus provide a good therapeutic effect.

It can be seen from the above disclosure that, with the infusion pumps provided in the embodiments of the present invention, an infusion interval input by the user and infusion doses intended for time points for infusion are received. Whenever an internal clock of the control unit 1 indicates that one of the time points for infusion is reached, a table lookup is performed to find the infusion dose corresponding to the reached time point. At last, an infusion is carried out based on the calculated infusion dose. This is compatible with the needs of physiological pulses and is therefore capable of regularizing the follicle-stimulating hormone (FSH) and luteinizing hormone (LH) pulse rhythms and hence regulating the patient's FSH and LH levels in a more effective manner.

Additionally, the infusion pumps according to the present invention enable pulsed subcutaneous infusions of HMG performed in a manner optimized according to the characteristics of sustained infusions, thereby allowing patients to restore the normal physiological function and, in particular, in the treatment of central hypogonadism, effectively helping those with pituitary dysfunction in sustained, accurate, intelligent medication and hence providing an enhanced therapeutic effect because of the compatibility with the physiological regulation mechanism of the thalamus-pituitary-gonadal axis.

Although details in implementation of the infusion pumps according to the present invention have been described above with the use of human menopausal gonadotropins as a medicament for the treatment of hypogonadotropic hypogonadism as an illustrative example, suitable medicaments according to the present invention include, but not limited to, human menopausal gonadotropins because those of ordinary skill in the art may also apply the infusion pumps to other medicaments for the treatment of hypogonadotropin hypogonadism based on the teachings of the preferred embodiments disclosed above.

The foregoing preferred embodiments of the present invention are presented merely to enable those skilled in the art to understand or carry out the present application. Various modifications to these embodiments are apparent to those skilled in the art, and the general principles defined herein may be embodied in other embodiments without departing from the spirit or scope of the present application. Accordingly, the present application is not limited to the embodiments disclosed herein, but rather it is intend to have the broadest scope consistent with the principles and novel features disclosed herein.

What is claimed is:

1. An infusion pump, comprising: a control unit, a container, an actuation unit and a detection unit, the control unit coupled to each of the actuation unit and the detection unit, the container coupled to each of the actuation unit and the detection unit,
   the container configured to store a medicinal liquid containing a medicament for treating hypogonadotropic hypogonadism, the control unit configured to receive an external control signal, the external control signal comprising an infusion interval, a concentration of the medicinal liquid and a dose of the medicament at each infusion, the control unit performing control based on the infusion interval such that the actuation unit is activated to cause the medicinal liquid to flow out of the container, the detection unit configured to detect an output of the medicinal liquid from the container and feed the output back to the control unit, the control unit configured to deactivate the actuation unit based on the dose of the medicament at each infusion, the concentration of the medicinal liquid and the fed-back output of the medicinal liquid;
   wherein time points for respective infusions are calculated from the infusion interval; and wherein the control unit, upon determining that one of the time points is reached, reads out one of the infusion doses that corresponds to the reached time point and performs control such that the actuation unit is activated to carry out an infusion action based on the read-out infusion dose;

wherein concurrently with the actuation unit carrying out the infusion action, the control unit reads out a next one of the infusion doses that corresponds to a next one of the time points and if the next infusion dose equals to an initial value, the control unit reads out a further next one of the infusion doses that corresponds to a further next one of the time points that is next to the next time point until one of the infusion doses, which is not equal to the initial value, is found, and a corresponding one of the time points that corresponds to the infusion dose, which is not equal to the initial value, is taken as a time point for a next infusion action; and if the infusion dose is not equal to the initial value, the control unit takes the next time point as a time point for the next infusion action.

2. The infusion pump of claim 1, wherein the medicament for treating hypogonadotropic hypogonadism is human menopausal gonadotropins; the medicinal liquid is a medicinal liquid of human menopausal gonadotropins; the infusion interval for the medicinal liquid of human menopausal gonadotropins is 90-120 minutes; the dose of human menopausal gonadotropins at each infusion is 0.04-0.2 μg/kg of body weight; and the concentration of the medicinal liquid of human menopausal gonadotropins is 75-225 μg/ml.

3. The infusion pump of claim 2, wherein the infusion interval for the medicinal liquid of human menopausal gonadotropins is 90 minutes; the dose of human menopausal gonadotropins at each infusion is 0.1-0.2 μg/kg of body weight; and the concentration of the medicinal liquid of human menopausal gonadotropins is 150-225 μg/ml.

4. The infusion pump of claim 1, wherein the actuation unit comprises a DC motor and a transmission mechanism; an outlet is provided on one end of the container and a piston is provided in the container; one end of the transmission mechanism is coupled to the piston and the other end is coupled to the DC motor; the transmission mechanism is configured to convert rotation motion of the DC motor to linear motion of the piston; and the piston is configured to move toward the outlet so that the medicinal liquid in the container is discharged from the outlet.

5. The infusion pump of claim 4, wherein the detection unit comprises a detection device for counting a number of rotations of the DC motor, which is coupled to a rotary shaft of the DC motor; the control unit calculates a number of theoretical rotations of the DC motor based on the dose of the medicament and the concentration of the medicinal liquid of the container, and feeds the number of theoretical rotations back to the detection device for counting the number of rotations of the DC motor; and the detection device for counting the number of rotations of the DC motor controls whether to deactivate the DC motor based on the fed-back number of theoretical rotations.

6. The infusion pump of claim 4, wherein the detection unit comprises a detection device for counting a number of rotations of the DC motor, which is coupled to a rotary shaft of the DC motor; the detection device for counting the number of rotations of the DC motor is configured to count a number of actual rotations of the DC motor and feed the number of actual rotations back to the control unit; and the control unit calculates a number of theoretical rotations of the DC motor based on the dose and the concentration of the medicinal liquid of the container, judges, based on the number of actual rotations, whether the DC motor already reaches the number of theoretical rotations, and if the condition is met, perform control such that the DC motor is deactivated.

7. The infusion pump of claim 1, wherein the actuation unit is an expulsion device which is coupled to one end of the container where the outlet is provided and is configured to expel the medicinal liquid out of the container.

8. The infusion pump of claim 7, wherein the expulsion device is a peristaltic pump, a piezoceramic pump or a film pump.

9. The infusion pump of claim 1, wherein the detection unit comprises a pressure sensor which is coupled to the container and configured to sense a pressure resulting from the flow of the medicinal liquid in the container and to feed the pressure back to the control unit; and the control unit obtains an output of the medicinal liquid at each time by looking up a table based on the pressure resulting from the flow of the medicinal liquid.

10. The infusion pump of claim 1, wherein the control unit comprises a storage unit and a clock unit; the control unit judges whether any one of time points for infusion is reached based on a timing function of the clock unit and the storage unit stores the time points for respective infusions and infusion doses of the medicament corresponding to the time points; and wherein the time points for respective infusions are calculated from the infusion interval.

11. The infusion pump of claim 10, wherein the control unit further comprises a predefined minimum time interval; and the infusion interval is a multiple of the minimum time interval.

12. The infusion pump of claim 11, wherein the storage unit comprises a storage table with a size of 2×n, where n is a product of dividing 24×60 by the minimum infusion interval measured in minutes; the storage table has a first row where theoretical time points for infusion are stored and a second row where initial values for the infusion doses of the medicament are stored; and upon receipt of the external control signal, the control unit converts the infusion interval to the time points for infusion, finds cells in the first row where the ones of the theoretical time points that are consistent with the converted time points for infusion are stored and writes the infusion doses in corresponding cells in the second row of the storage table.

13. The infusion pump of claim 1, wherein the infusion pump further comprises an input unit coupled to the control unit; and the external control signal is input to the control unit through the input unit.

14. The infusion pump of claim 1, wherein the infusion pump further comprises a casing in which the control unit, the container, the actuation unit and the detection unit are accommodated.

* * * * *